(12) United States Patent
Arnal et al.

(10) Patent No.: US 8,579,797 B2
(45) Date of Patent: Nov. 12, 2013

(54) METHODS AND APPARATUS FOR SECURING AND TENSIONING A URETHRAL SLING

(75) Inventors: Kevin R. Arnal, Excelsior, MN (US); W. Kyle Knauf, McKinney, TX (US)

(73) Assignee: AMS Research Corporation, Minnetonka, MN (US)

(*) Notice: Subject to any disclaimer, the term of this patent is extended or adjusted under 35 U.S.C. 154(b) by 1065 days.

(21) Appl. No.: 12/494,963

(22) Filed: Jun. 30, 2009

(65) Prior Publication Data

US 2009/0264698 A1 Oct. 22, 2009

Related U.S. Application Data

(62) Division of application No. 11/381,668, filed on May 4, 2006, now abandoned.

(60) Provisional application No. 60/677,456, filed on May 4, 2005.

(51) Int. Cl.
*A61F 2/00* (2006.01)

(52) U.S. Cl.
USPC .............................. 600/30; 600/37

(58) Field of Classification Search
USPC .................. 600/29–31, 37; 606/151–158
See application file for complete search history.

(56) References Cited

U.S. PATENT DOCUMENTS

| | | | |
|---|---|---|---|
| 5,370,661 A | 12/1994 | Branch | |
| 5,474,543 A | 12/1995 | McKay | |
| 6,042,534 A | 3/2000 | Gellman et al. | |
| 6,042,536 A | 3/2000 | Tihon et al. | |
| 6,221,005 B1 | 4/2001 | Bruckner et al. | |
| 6,334,446 B1* | 1/2002 | Beyar | 128/898 |
| 6,382,214 B1 | 5/2002 | Raz et al. | |
| 6,406,480 B1 | 6/2002 | Beyar et al. | |
| 6,506,190 B1 | 1/2003 | Walshe | |
| 6,589,249 B2 | 7/2003 | Sater et al. | |
| 6,641,524 B2 | 11/2003 | Kovac | |
| 6,648,921 B2* | 11/2003 | Anderson et al. | 623/23.64 |
| 6,652,450 B2 | 11/2003 | Neisz et al. | |
| 6,773,450 B2 | 8/2004 | Leung et al. | |
| 7,175,591 B2 | 2/2007 | Kaladelfos | |
| 2002/0183762 A1 | 12/2002 | Anderson et al. | |
| 2003/0069469 A1 | 4/2003 | Li | |
| 2004/0106845 A1 | 6/2004 | Anderson et al. | |
| 2004/0106847 A1 | 6/2004 | Benderev | |

(Continued)

FOREIGN PATENT DOCUMENTS

WO WO 2005/122954 12/2005

*Primary Examiner* — Charles A Marmor, II
*Assistant Examiner* — Catherine E Burk
(74) *Attorney, Agent, or Firm* — Kagan Binder, PLLC

(57) ABSTRACT

Improved methods and apparatus to secure a urethral sling to pubic bone in a sub-urethral location to support the urethra and alleviate incontinence are disclosed. The urethral sling is preferably formed of a flexible sheet material extending between opposed first and second sling ends and bounded by opposed first and second sling sides. The urethral sling is selectively tensioned in a central portion intermediate the first and second sling ends and/or in one or both of end portions bracketing the central portion. In one embodiment, pre-positioned plicating lines in the central portion are selectively drawn and tied to slacken the central portion and tension the end portions. In further embodiments, bone anchor lines passed through locations displaced from the sling ends are drawn and fixed to tension the central portion between the displaced locations and slacken the end portions.

3 Claims, 8 Drawing Sheets

(56) References Cited

U.S. PATENT DOCUMENTS

| | | | |
|---|---|---|---|
| 2006/0009673 A1* | 1/2006 | Chan | 600/29 |
| 2006/0089525 A1* | 4/2006 | Mamo et al. | 600/37 |
| 2006/0247490 A1* | 11/2006 | Merade et al. | 600/30 |

* cited by examiner

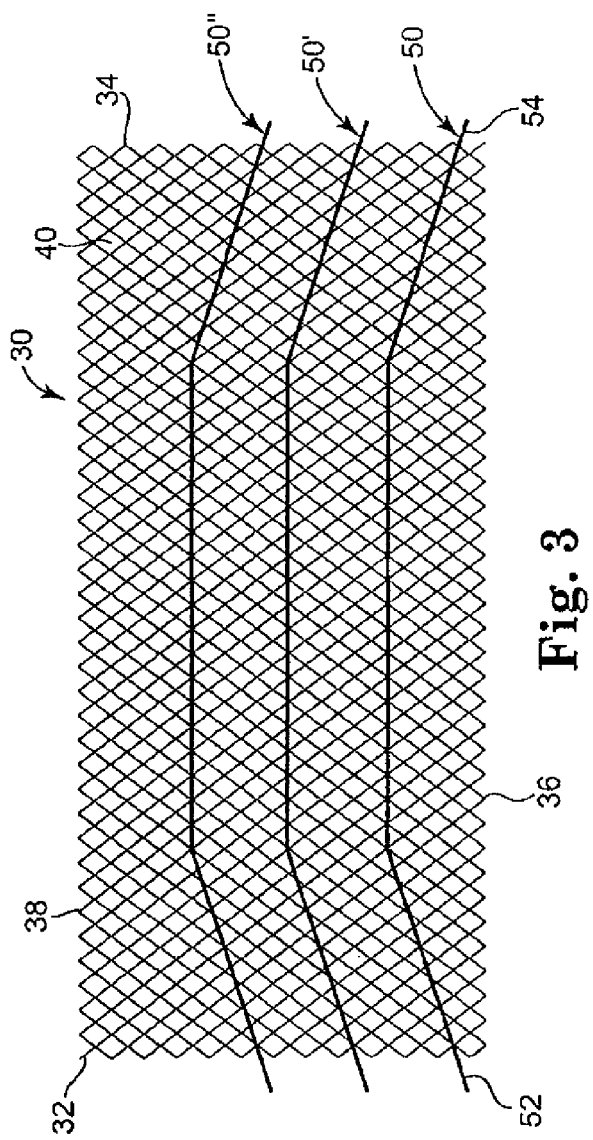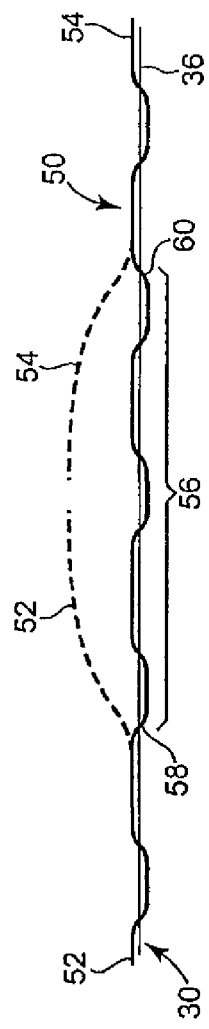

METHODS AND APPARATUS FOR SECURING AND TENSIONING A URETHRAL SLING

RELATED APPLICATIONS

This application is a division of U.S. Ser. No. 11/381,668, filed May 4, 2006, titled METHODS AND APPARATUS FOR SECURING AND TENSIONING A URETHRAL SLING TO PUBIC BONE, by Amal et al., which claims priority to U.S. Provisional Application Ser. No. 60/677,456 filed May 4, 2005, the entireties of both applications being incorporated herein by reference.

FIELD OF THE INVENTION

The present invention pertains to surgical procedures, kits, and implants to alleviate human incontinence, and particularly to improved methods and apparatus to secure a urethral sling to pubic bone in a sub-urethral location and tensioning the urethral sling to support the urethra and alleviate incontinence.

BACKGROUND OF THE INVENTION

Incontinence is a condition characterized by involuntary loss of urine, beyond the individual's control, that results in the loss or diminution of the ability to maintain the urethral sphincter closed as the bladder fills with urine. Male or female stress urinary incontinence (SUI) occurs when the patient is physically or emotionally stressed.

One cause for this condition is damage to the urethral sphincter or loss of support of the urethral sphincter, such as can occur in males after prostatectomy or following radiation treatment, or that can occur due to pelvic accidents and aging related deterioration of muscle and connective tissue supporting the urethra. Other causes of male incontinence include bladder instability, over-flowing incontinence and fistulas.

The female's natural support system for the urethra is a hammock-like supportive layer composed of endopelvic fascia, the anterior vaginal wall, and the arcus tendineus (a distal attachment to the pubic bone). Weakening and elongation of the pubourethral ligaments and the arcus tendineus fascia pelvis, weakening of the endopelvic fascia and pubourethral prolapse of the anterior vaginal wall, and their complex interaction with intraabdominal forces are all suspected to play a role in the loss of pelvic support for the urethra and subsequent hypermobility to an unnaturally low non-anatomic position, leading to urinary incontinence.

Females can also exhibit cystocele, a condition due to laxity of the pelvic floor wherein the bladder extrudes out and downwards causing SUI. The severity of this bladder collapse is rated between Grades one through four. In Grade four cystocele, the bladder extrudes out of the vaginal opening. The treatment of choice for this condition includes the reduction or closing of the pelvic floor opening from which the bladder descends using sutures. As noted below, other procedures involving implantation of a urethral sling are also gaining acceptance.

In general, continence is considered to be a function of urethral support and coaptation. For coaptation to successfully prevent or cure incontinence, the urethra must be supported and stabilized in its normal anatomic position.

The present application is directed to the treatment of SUI and chronic urinary incontinence due to inability of the urethral sphincter to close or remain closed as bladder fluid pressure builds. Currently, incontinence treatments of choice involve implantation of a Kaufman Prosthesis, an artificial sphincter (such as the AMS-800 Urinary Control System available from American Medical Systems, Inc.), or a urethral sling procedure in which a urethral sling is inserted beneath the urethra and advanced in the retro pubic space. Peripheral portions of the elongated urethral sling are affixed to bone or body tissue, and a central portion of the elongated urethral sling extends under the urethral or bladder neck to provide a platform that compresses the urethral sphincter, limits urethral distention, and pelvic drop, and thereby improves coaptation.

Male and female urethral sling procedures are disclosed in commonly assigned U.S. Pat. Nos. 6,406,480, 6,652,450 and 6,382,214, for example, and further female urethral sling procedures are described in commonly assigned U.S. Pat. No. 6,641,524, for example, and publications and patents cited therein. The implantation of certain urethral slings involves the use of delivery systems configured for and techniques that involve transvaginal, transobturator, supra-pubic and pre-pubic exposures or pathways.

The above-referenced '214 and 480 patents describe apparatus and methods for treatment of male incontinence and female cystocele repair in which a urethral sling material is positioned between the descending pubic rami of the pubic bone. In such an operation a "hammock-like" urethral sling material is sutured below the urethra in males, or below the posterior bladder wall in the case of cystocele in females. The urethral sling material may comprise synthetic material or cadaveric or autologous fascia and may or may not be absorbable over time.

In the male case, the urethral sling applies passive compression against the bulbar urethra. The compression, either by itself or in conjunction with urethral mobility, prevents urine leak during strain. If additional passive pressure is required on the urethra after surgery is completed, collagen or other bulky material can be injected with a tiny needle through the perineum, causing more pressure created by the bulky material on one side (the lower or caudal side) by the urethral sling, and on the other (the upper or superior) side compressing the urethra. An example of a urethral sling sutured to and extending between four bone anchors or screws fixed to the descending pubic rami is depicted in FIG. 12 of the above-referenced '214 patent.

One minimally invasive surgical procedure that incorporates the teachings of the above-referenced '214 patent to alleviate mild to moderate male SUI is performed employing the InVance™ Male Urethral Sling System for implanting the InteMesh™ Synthetic Surgical Mesh (both available from American Medical Systems, Inc.) in a manner generally described in the above-referenced '214 patent. The InteMesh™ Synthetic Surgical Mesh is about 4 cm×7 cm and knitted from a supple polyester material coated with silicone, the knitted mesh having a pore size that allows for tissue ingrowth during chronic implantation. The InVance™ Male Urethral sling System includes four to six, typically, titanium bone anchors or screws and a disposable, battery powered, inserter or driver. Each bone screw has a distal self-tapping spiral thread and a length of No. 1 Prolene suture extending proximally from the bone screw.

In the implantation procedure, the patient is first placed in the lithotomy position and draped, and the surgical field is prepared. A 16 French Foley catheter, for example, is inserted into the urethra, the catheter balloon is inflated t to assist the surgeon in identifying the urethra during dissection, and the scrotum is elevated. A vertical incision is made over the midline in the perineum, and the skin and subcutaneous tissues are dissected free. The bulbocavernous muscle is then exposed, and dissection is carried out posteriorly to the area of the transverse perineum to completely free the bulbar urethra. Lateral dissection is used to expose the corpora cavernosum and the descending pubic rami.

The six titanium bone screws are then screwed, one at a time, into the inner portion of the descending pubic rami of the pubic bone using the battery-powered driver. The bone screws are screwed fully into the pubic bone so that the No. 1 Prolene sutures extend outward from each bone. The location of each bone screw and the order of bone screw insertion can be selected by the surgeon. In one approach, the first pair of bone screws is inserted just below the symphysis, the second pair is inserted just proximal to the level of the ischial tuberosity, and the third pair is inserted intermediate the first and second pair.

The InteMesh™ Synthetic Surgical Mesh is then applied against the array of bone screws bridging the lower surface of the bulbar urethra between the descending pubic rami to determine where the sutures will be passed through the mesh pores and tied off. The sutures extending from one of the descending pubic rami may be first passed though selected mesh pores and tied off employing several surgeon's suture knots. Tension is then applied to the other side or end of the urethral sling as it is drawn against the other pubic pubic ramus to determine where the bone screw sutures should be passed through the mesh pores and tied off.

The determination of the appropriate tension may be accomplished using a cough test or Retrograde Perfusion Pressure (RPP) test. To perform a RPP test, the Foley catheter balloon is then deflated, and the Foley catheter is withdrawn and connected to a sterile saline perfusion line. A zero pressure state is obtained by lowering the bag to the level of the symphysis. The tip of the catheter is repositioned at the penoscrotal angle, and the urethral resistance to start of flow or leakage is recorded (by distance of the bag above the level of the symphysis). In patients under anesthesia suffering from sphincter incontinence, the urethral resistance is very low. Tension is then applied to the untied side of the urethral sling by advancing the end of the urethral sling along the sutures toward the bone screws so that the urethral sling bears against the bulbar urethra. The mesh urethral sling compresses the bulbar urethra as it is adjusted in tension to increase urethral resistance to withstand a pressure selected between 30 and 60 cm of water. The sutures are then tied to maintain the selected tension.

The Foley catheter is then advanced to the bladder (which should advance without difficulties), and the wound is irrigated with Bethadine solution and closed in layers. Subsequently, the Foley catheter is removed after 2 hours, and the patient can be discharged home on oral antibiotics and pain medication after completing a successful voiding trial.

The above-referenced '214, '480, and '524 patents also disclose procedures for repairing a cystocele using retropubic and lateral pubic bone anchors. The surgery disclosed in the '214 patent is indicated for patients with grade four cystocele and urethral hypermobility. The procedure repairs the central defect, the lateral detect, approximates the cardinal ligaments to the midline, and creates a urethral sling of the urethra.

After preparation and draping, a Foley catheter is inserted in the bladder. Once the catheter is in place, a "goal post" incision is made. The vertical bars of the goal post extend laterally from the distal urethra to the horizontal bar that is made just proximal to the bladder neck. The vertical bars reach the vaginal cuff.

After creation of the goal post incision, the vaginal wall is dissected free to expose the perivesical fascia laterally and the cardinal ligaments posteriorly. A figure eight 2-0 absorbable suture is applied to approximate the cardinal ligament to the midline without tying it. If an enterocele sac is encountered, it should be repaired at this stage.

The retropubic space is then entered over the periurethral fascia at the level of the vertical bars of the incision, and the urethropelvic ligaments are exposed. Two fascial anchors (the upper pair) are inserted into the tissue of the suprapubic area. These anchors may comprise a bone screw having a distal self-tapping screw thread of the type described above with a No. 1 Prolene suture attached to the proximal end of the bone screw. Other types of bone anchors are disclosed in the above-referenced '480 patent.

In an alternative embodiment, at this stage of the procedure, the retropubic space is not open and two bone anchors or screws of the type described above are applied to the inner surfaces of the symphisis using a right angle drill.

After application of the first set of anchors, a second pair of bone anchors or screws of the types described above and in the above-referenced '480 patent are applied to the inner surface of the descending pubic rami of the symphysis.

Once the four bone screws are in place, the bladder prolapse is reduced using a moist sponge over a right angle retractor. Alternatively, a Dexon mesh is applied and left in place. The lower pair of Prolene sutures are then used to incorporate the perivesical fascia and the cardinal ligaments area. Interrupted 2-0 absorbable sutures are used to approximate the perivesical fascia to the midline over the Dexon mesh.

A variation on this procedure is set forth in commonly assigned, U.S. Patent Application Publication No 2002/0183762 to provide urethral support and coaptation employing the InFast™ Ultra Transvaginal Urethral sling System for implanting a urethral sling selected from among the InteXen™ Porcine Dermal Matrix or the InteDerm™ Allograft Dermal Matrix or the InteLata™ Allograft Fascia Lata (all available from American Medical Systems, Inc.). The selected urethral sling is intended to be cut to size and in a T-shape to fit between the bone screws and to be attached thereto as described above. The InFast™ Ultra Female Urethral sling System includes four, typically, titanium bone screws and a disposable, battery powered, inserter that positively engages the bone screw to drive it into bone. In this system, a length of No. 1 Prolene suture is passed through a metal ring extending proximally from the bone screw, and the ends of the suture are joined to needles adapted to be passed through the urethral sling. A distal end of a drive shaft of the battery-powered inserter engages the bone screws, and the drive shaft is shaped to enable orientation of the screw threads toward the posterior aspect of the pubic bone.

The tensioning of the selected urethral sling is accomplished in this procedure as the suture needles are passed through the urethral sling, and the urethral sling is pressed against the bone surface. The suture needles are severed, and the suture ends are tied together. The tied suture knot is slid upward and posteriorly (behind the bone) to ensure juxtaposition of the sling end to the bone surface.

The above-described bone screws are intended to be driven into the bone until completely embedded with the suture extending out of the self-tapped bore in the bone.

Thus, in the above-described procedures, the urethral sling in maintained in place, and sling tension is adjusted and applied through the tied sutures. The procedure of initially tensioning and tying the sutures takes an undue amount of the surgical time, up to 15-25 minutes as observed in some instances employing the InVance™ Male Urethral Sling System for implanting the InteMesh™ Synthetic Surgical Mesh. Moreover, it is sometimes difficult to achieve the tension in the urethral sling that is sufficient to constrict the urethral sphincter to provide urethral resistance to leakage at the selected water bag height, e.g. at 60 cm.

It would be desirable to simplify the process of and to reduce the amount of time that it takes to tension and secure the urethral mesh to the sutures extending from bone anchors of the types described above.

If the resulting sling tension is not adequate, it may be necessary to untie the tied sutures to readjust tension including possibly repositioning the bone anchor in the pubic bone or the sutures extending through the urethral sling. Tying, untying and retying the suture knots consumes further time. Thus, it would be desirable to simplify the process of and to reduce the amount of time that it takes to detach, adjust tension, and reattach the urethral mesh to the sutures extending from bone anchors.

Moreover, the sutures may have been trimmed at the knot following an earlier tying. Applying tension through and retying the trimmed sutures may be difficult to accomplish. Therefore, it would be desirable to simplify the process of tensioning the sutures in a manner that does not require untying and retying the sutures and is not compromised by trimming the suture length.

SUMMARY OF THE INVENTION

The preferred embodiments of the present invention incorporate a number of inventive features that address the above-described problems that may be combined as illustrated by the preferred embodiments or advantageously separately employed. It will be understood that the inventive features and preferred embodiments may be applied in treating both male and female patients.

In one aspect of the present invention, a urethral sling is preferably formed of a flexible sheet material extending between opposed first and second sling ends and bounded by opposed first and second sling sides. The urethral sling is provided with at least one pre-positioned, plicating line, e.g., a suture, having a plicating line length extending between first and second plicating line free ends. An intermediate portion of the plicating line is passed through the material of the urethral sling between at least first and second points disposed intermediate first and second sling ends. The intermediate portion of the pre-positioned, plicating line thus extends generally across a central portion of the urethral sling displaced from the first and second sling ends.

In use, the urethral sling is affixed by any of the known techniques to the bone screws or anchors inserted into the pubic bones to extend laterally across and support the urethra, and testing for urethral resistance to leakage may be conducted. The plicating line free ends of the one or more pre-positioned plicating line may be gripped and drawn together to draw a fold or crease in the sling material (i.e., to plicate the sling material) in the central portion of the urethral sling, whereby the urethral sling material is drawn tight in first and second end portions bracketing the central portion. Thus, the urethral sling is tensioned by the tension of the plicating line against the urethra to increase urethral resistance to leakage. The resistance to leakage may be rechecked, and the plicating line free ends tied together to maintain the slack or fold or crease and resulting sling tension that provide an acceptable urethral resistance to leakage.

In preferred embodiments, the length of plicating line may be passed through the material of the urethral sling at further points intermediate the first and second points. In addition, the plicating line free ends may be folded against one side of the urethral sling and held there to avoid entanglement during or interference with the procedure. The plicating line free ends are held in place by threading through additional suture pores until released for use.

In further preferred embodiments, more than one plicating line is provided extending across the central portion of the urethral sling so that the urethral sling may be tensioned more precisely between the first and second sling sides. Unused plicating lines may be left in place or retracted from the urethral sling.

In a further aspect of the present invention usable separately or together with the above-described aspect of the invention, anchor fixation lines extending from each bone anchor are employed alone or in conjunction with line retainers to affix an implantable medical device in the patient's body. Each bone anchor comprises a bone anchor body having a bone fixation end and an elongated bone anchor line affixed at one line end to the bone anchor body and extending to an anchor line free end.

In one variation, the anchor line comprises at least one line fixation element shaped to be fitted with the device fixation element to affix the medical device to the bone anchor. In other variations, the anchor lines comprise a plurality of line fixation elements spaces along the anchor line length to be selectively fitted to the device fixation element.

In the context of implanting a urethral sling formed of a mesh fabric, the device fixation element comprises a selected mesh pore. In this aspect of the invention, each bone anchor line is inserted through the sling material at a location of the urethral sling displaced from a sling end and the site where the bone anchor is affixed into the pubic bone. Generally speaking, the bone anchor line or line pair extends from each bone anchor affixed to one pubic bone toward a bone anchor affixed to the other pubic bone and is passed through the sling material at the displaced location. In preferred embodiments, the bone anchor lines are in this way extended across first and second end portions of the urethral sling and passed through the sling material at the displaced locations, whereby the central portion of the urethral sling is bounded by the displaced locations. The bone anchor lines are selectively tensioned and fixed at the displaced locations to slacken and possibly induce a fold or crease or plication in the first and/or second end portions and tension the central portion.

In one preferred embodiment, a line retainer is provided that can be selectively advanced over the bone anchor line extending through the mesh and against the urethral sling to maintain the tension. In preferred embodiments, the line retainer is resilient and has a retainer bore sized and shaped to be expanded to pass over the bone anchor line (including any outwardly extending line fixation elements) as the retainer is advanced toward the bone anchor and that resists retraction over the bone anchor away from the bone anchor. Retainer-dispensing tools may be provided that facilitate application of the retainers over the anchor lines.

After adequate tension is achieved with or without use of line retainers, the anchor lines may be tied off with fewer or smaller knots to reduce suturing time, and the final exposed line trimmed.

It will be understood that the present invention may be practiced employing any suitable bone anchor line and bone anchors of any of the types known in the prior art, including those disclosed in the above-referenced '480 patent.

Advantageously, the procedure for attaching the urethral sling to bone anchors is simplified to shorten the surgical time, the tensioning and fixation are made more reliable, and any line knots that are employed are reduced in size.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 3 is a plan view of an embodiment of a urethral sling in accordance with the present invention with one or more pre-positioned plicating line extending across the urethral sling;

FIG. 4 is a side view of the urethral sling of FIG. 3;

Figure 1:
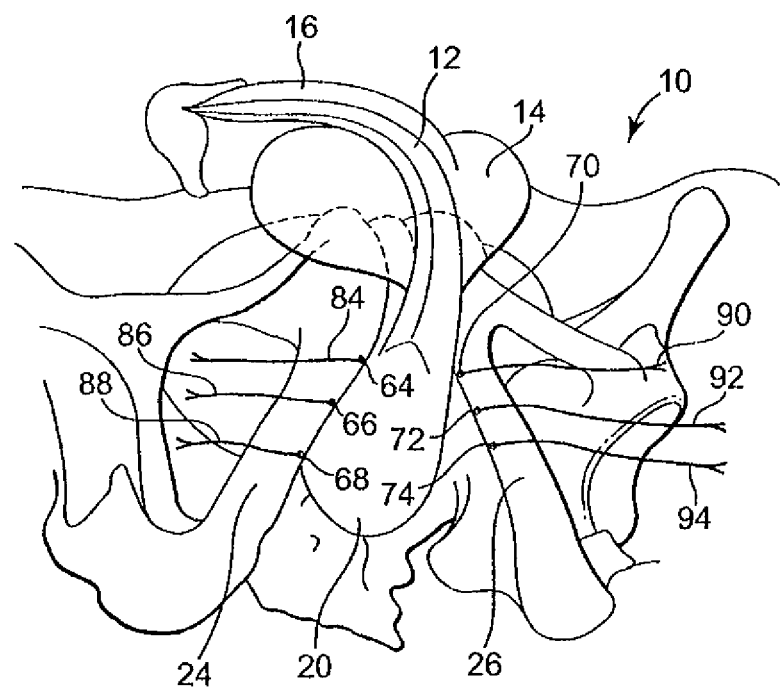
FIG. 1 is a schematic illustration of the fixation of bone anchors or screws to descending pubic rami with lines extending from the bone screws.

It will be understood that the drawing figures are not necessarily to scale.

DETAILED DESCRIPTION OF PREFERRED EMBODIMENTS

In the following detailed description, references are made to illustrative embodiments of methods and apparatus for carrying out the invention. It is understood that other embodiments can be utilized without departing from the scope of the invention. Preferred methods and apparatus are described for tensioning urethral slings fixed to pubic bones. It will be understood that the term "urethral sling" encompasses any type of sling, tape, hammock or the like that supports and or/applies compression to the urethra. The urethral sling may be formed of any biocompatible flexible sheet material known in the art with or without pores or openings through the sheet material.

For convenience of illustration of the aspects of the present invention, the preferred embodiments simply depict the bone anchors as bone screws. It will be understood that the present invention may be practiced employing bone anchors of any of the types known in the prior art, e.g., those disclosed in the above-referenced '480 patent.

For convenience of illustration of the aspects of the present invention, the preferred embodiments are described in the context of implantation of a urethral sling in a male patient. It will be understood that the present invention is not so limited and may also be practiced in the implantation of urethral slings in female patients.

It will be understood that the fixation lines and plicating lines disclosed herein may be but are not necessarily formed of lengths of suture.

Figure 2:
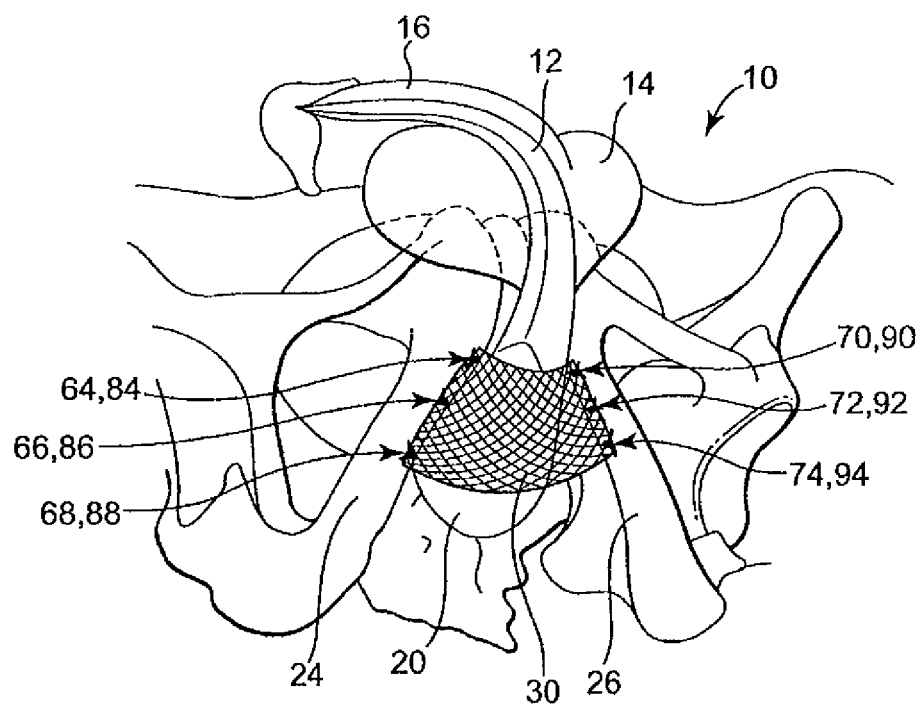
FIG. 2 is a schematic illustration of the fixation of a urethral sling to the bone screws with the lines extending from the bone screws in accordance with the prior art resulting in insufficient tensioning in certain instances.

Referring to FIGS. 1 and 2, the male anatomy in the pelvic region 10 is depicted schematically to illustrate how a urethral sling 30 is affixed to the right and left descending pubic rami 24 and 26 to extend across and support the male urethra 12 in the manner described above, for example, in the procedure employing the InVance™ Male Urethral Sling System for implanting the InteMesh™ Synthetic Surgical Mesh urethral sling.

An embodiment of an improved urethral sling 30 of the present invention, which can be implemented in the InteMesh™ Synthetic Surgical Mesh urethral sling, is depicted in greater detail in FIGS. 3 and 4. In a preferred embodiment, the urethral sling 30 is knitted from a supple polyester yarn to have a plurality of sling or mesh pores 40 and is coated with medical grade silicone rubber. The knitted mesh pores 40 have a pore size that allows for tissue ingrowth therethrough during chronic implantation. The urethral sling 30 extends end-to-end between first and second sling ends 32 and 34 and side-to-side between first and second sling sides 36 and 38. At least one plicating line 50 having a line length extending between first and second line free ends 52 and 54 is fitted through mesh pores 40. An intermediate line portion 56 is passed through two or more mesh pores 40 to extend the line length between points 58 and 60 across the urethral sling 30 intermediate the first and second sling ends 32 and 34 and either parallel to or at an angle to the first and second sling sides 36 and 38.

In preferred embodiments, the intermediate portion 56 of plicating line 50 may be passed through further pores 40 of the urethral sling 30 at points intermediate the first and second points 58 and 60. The line free ends 52 and 54 may be folded against one side of the urethral sling 34 and held there by passing them through additional pores as shown in FIG. 4. The line free ends 52 and 54 are released from the Additional plicating lines 50' and 50", for example, are depicted in FIG. 3 passing through the mesh pores 40 in the manner described above providing an exemplary illustration of a further preferred embodiment of a urethral sling 30.

Returning to FIGS. 1 and 2, as noted above, the surgical field is prepared after the patient, placed in the dorsal lithotomy position and draped. The scrotum 14 and penis 16 are elevated, a vertical incision is made over the midline in the perineum of the skin and subcutaneous tissues (not shown) are dissected to the side to expose the bulbocavernous muscle 20. Lateral dissection is used to expose the corpora cavernosum 22 and the surfaces of the descending pubic rami 24 and 26.

Figure 5:
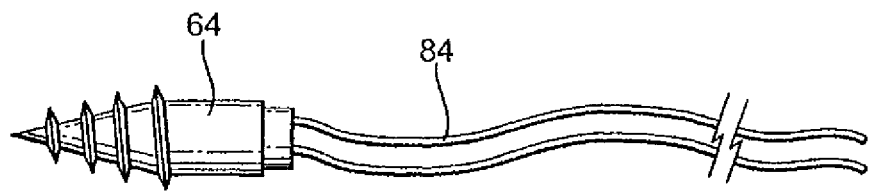
FIG. 5 is an expanded side view of a bone anchor, particularly a bone screw of the type employed in FIGS. 1 and 2, with a pair of bone screw lines extending from the screw body.

As shown in FIG. 1, the illustrated fixation of the surgical urethral sling 30 is effected employing six titanium bone screws 64, 66, 68, 70, 72, 74 sequentially driven by a disposable, battery powered, inserter or driver (not shown). Each bone screw 64, 66, 68, 70, 72, 74 has an anchor or screw body with a distal, self-tapping, spiral thread adapted to be screwed into bone when the screw tip is applied to the bone surface and the driver is powered. A pair of No. 1 Prolene suture lines 84, 86, 88, 90, 92, 94 extend proximally from each bone screw 64, 66, 68, 70, 72, 74, respectively. One such bone screw 64 with the pair of bone screw lines 84 extending from the screw body is depicted in the expanded view of FIG. 5. Typically, the pair of bone screw lines is crimped at one end into a bore of the bone screw and extends about 30 cm to bone screw line free ends. The bone screw line free ends can be joined as by use of ultrasonic welding to ease in handling and use of a bone screw fixation tool. The surgeon may choose to pass the joined line free ends through a selected mesh pore, tie a knot or knots, and then trim the lines. Or, the surgeon may first trim the lines, separately pass the severed line free ends through a common or separate mesh pores, tie a knot or series of knots, and again trim the line free ends.

The bone screws 64, 66, 68, 70, 72, 74 are screwed fully into the bone of the so that the No. 1 Prolene lines 84, 86, 88, 90, 92, 94, respectively, extend outward of the descending pubic rami 24 and 26 as shown in FIG. 1. The surgeon can select the location of each bone screw 64, 66, 68, 70, 72, 74 and the order of insertion. In one approach depicted in FIG. 1, a first pair of bone screws 64, 70 is inserted just below the symphysis, the second pair 66, 72 is inserted proximal to the level of the ischial tuberosity, and the third pair 68, 76 is inserted intermediate the first and second pair.

The urethral sling 30 is then applied against the array of bone screws 64, 66, 68, 70, 72, 74 bridging the lower surface of the bulbar urethra 20 between the descending pubic rami 24 and 26 to determine where each line of the respective line pairs 84, 86, 88, 90, 92, 94 will be passed through mesh pores.

The free ends of each line of each line pair 84, 86, 88, 90, 92, 94 are sequentially grasped, passed through separate mesh pores and drawn tight and tied together against the mesh of the urethral sling 30.

The lines of the line pairs 84, 86, 88 extending from the descending pubic ramus 24 may be first passed though selected mesh pores adjacent the first sling end 32. The first sling free end 32 is then pressed against the descending pubic ramus 24. The free ends of each line of each line pair 84, 86, 88 are sequentially grasped, drawn tight and tied together at least two times forming several surgeon's line knots against the mesh of the urethral sling 30 firmly holding the sling first end against the descending pubic ramus 24.

Tension is then applied to the second sling end 34 of the urethral sling 30 as it is drawn against the second pubic ramus 26 to determine where the lines of the bone screw line pairs 90, 92, 94 should be passed through mesh pores and tied off in the manner described above. Testing for urethral resistance to leakage may be conducted employing the techniques and instruments described above as the lines of bone line pairs 90, 92, 94 are drawn tight against the fabric of urethral sling 30 and tied off. The lines of bone line pairs 90, 92, 94 may be retracted from the initially selected pores 40 and reinserted in other pores 40 in the process of optimizing the tension. In this way, the urethral sling 30 is eventually lined to all of the bone anchors or screws 64, 66, 68, 70, 72, 74 inserted into the descending pubic rami 24 and 26 to extend laterally across and support the bulbar urethra 20. An intermediate portion of the urethral sling 30 extends between the bone screws 64, 66, 68 and the bone screws 70, 72, and 74.

The testing for urethral resistance may reveal that tension applied by the intermediate portion of the urethral sling 30 to the urethra 12 is insufficient to halt leakage despite the attempts to optimize urethral resistance. This deficiency and the preceding urethral resistance optimization tests and efforts may be advantageously minimized by taking the further steps of freeing the line free ends 52 and 54 of the plicating. line(s) 50, 50', 50" from the retained position shown in solid lines in FIG. 4 toward one another as shown in broken lines in FIG. 4 and tying them together with one or more surgeon's knot.

Figure 6:
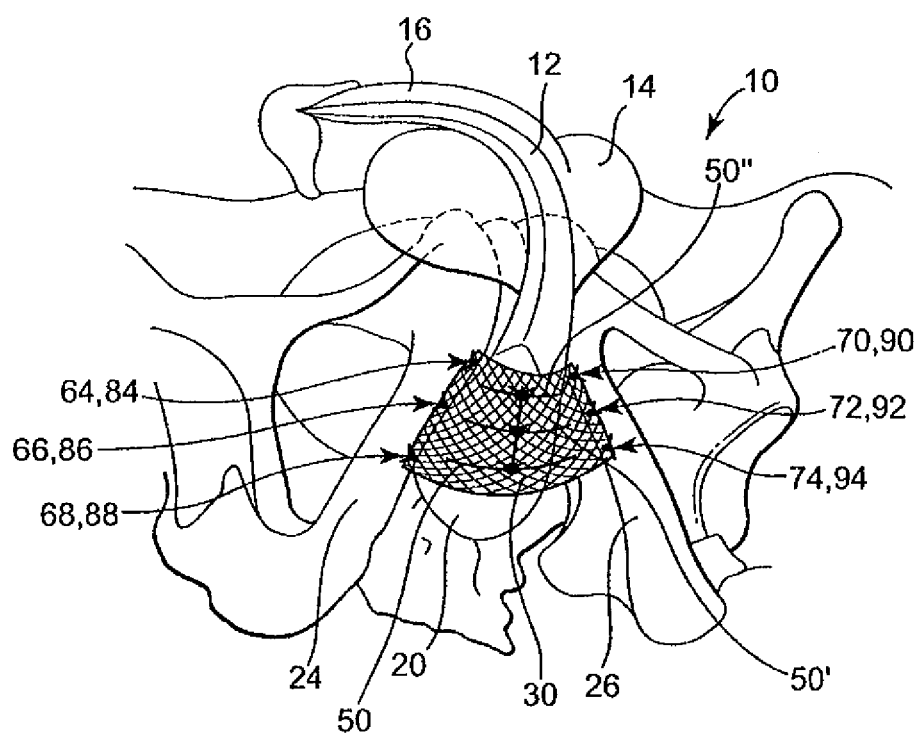
FIG. 6 is a schematic illustration of the urethral sling fixed to the bone screws with the plicating line(s) of the urethral sling of FIG. 3 drawn and tied to form a fold or crease in the urethral sling to adjust tension and obtain satisfactory urethral resistance.

More particularly, the plicating line free ends 52 and 54 may be gripped and drawn together after being freed from retention to shorten the distance between the first and second points, thereby shortening a dimension of the urethral sling 30 and tensioning it against the urethra 12 to increase urethral resistance to leakage. The resistance to leakage may be rechecked, and the plicating line free ends 52 and 54 tied together to maintain the shortened dimension and tension that provides an acceptable urethral resistance to leakage. The knotted plicating line free ends 52, 54 of each of the plicating lines 50, 50', 50" are shown overlying the mesh of the urethral sling 30 in FIG. 4. As also shown in FIG. 6, a mesh fold is created in the central portion as the urethral sling 30 is tensioned by the tied together, plicating line free ends 52, 54.

In this way, the pre-positioned plicating lines 50, 50' 50" slacken or draw a fold or crease in the sling material in the central portion of the urethral sling 30, whereby the urethral sling material is drawn tight in first and second end portions bracketing the central portion. Thus, the urethral sling 30 is tensioned by the tension of the plicating lines 50, 50', 50" against the urethra to increase urethral resistance to leakage. The resistance to leakage may be rechecked, and the plicating line free ends tied together to maintain the slack or fold or crease and resulting sling tension that provide an acceptable urethral resistance to leakage.

Unused plicating lines among lines 50, 50', 50" may be left in place or withdrawn from the mesh pores 40 of the urethral sling 30 and disposed of.

The tensioning of a urethral sling, e.g., the InteMesh™ Synthetic Surgical Mesh urethral sling or the above-described urethral sling 30 can be enhanced in a further way. For convenience, the urethral sling 30 will be employed in describing the following embodiments, but it understood that the plicating lines 50, 50', 50" may be absent or may be employed in the manner described above to augment tensioning of the urethral sling 30.

In these embodiments, each bone screw (or other bone anchor) line is inserted through a selected mesh pore 40 in a portion or at a location of the urethral sling 30 displaced from the site where the bone screw is screwed into the descending pubic ramus and intermediate the sling first and second ends 32 and 34. The urethral sling 30 is urged toward each bone screw screwed into the descending pubic ramus to slacken or form a fold or crease in the end portion of the urethral sling 30 between the bone screw and the selected mesh pore 40 that tensions the central portion of the urethral sling 30. In the following description of this aspect of the invention, it will be understood that either or both of the end portions of the urethral sling 30 can be made slack or have a fold or crease induced therein.

Thus, in the embodiment of this aspect of the invention illustrated in FIGS. 7-10, the bone screws 64, 66, 68 are screwed into the descending pubic ramus 24 and the bone screws, 70, 72, 74 are screwed into the descending pubic ramus 26 in the manner depicted in FIG. 1 and described above. The bone line pairs 84, 86, 88, 90, 92, 94 (or a single line) extend from the respective bone screw 64, 66, 68, 70, 72, 74 as also shown in FIG. 1.

Figures 7, 8:
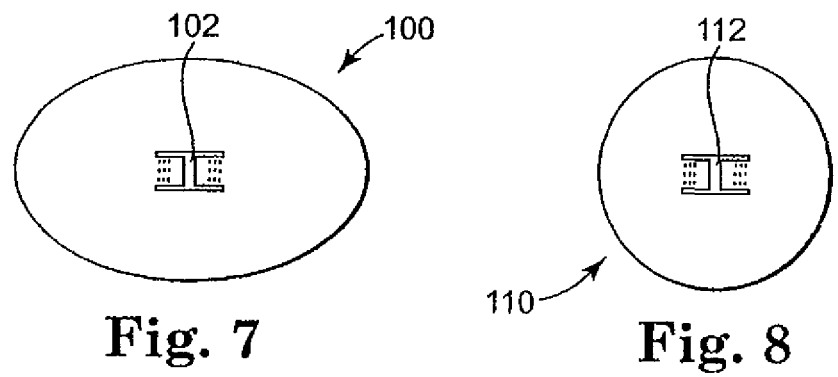
FIG. 7 is a plan view of an embodiment of a line button adapted to be applied over the lines extending from the bone screw of FIG. 5.
FIG. 8 is a plan view of a further embodiment of a line button adapted to be applied over the lines extending from the bone screw of FIG. 5.

In accordance with this embodiment, a line retainer, e.g., one of the line button 100 depicted in FIG. 7 or the line button 110 depicted in FIG. 8, is provided for fixation of each bone line pair 84, 86, 88, 90, 92, 94 extending through a selected mesh pore 40. The line buttons 100 and 110 have a thickness and lateral dimension, e.g., the major and minor diameters of the ellipse shaped line button 100 and the diameter of the circular line button 110 that are suitable for implantation at the site and cannot be passed through a mesh pore 40 at the elastic limits of the yarn forming the urethral sling 30. It will be understood that the line retainers may have any shape and size suitable for the purposes of applying retaining force against a portion of the urethral sling 30 and resisting passage through a mesh pore 40.

Figure 9:
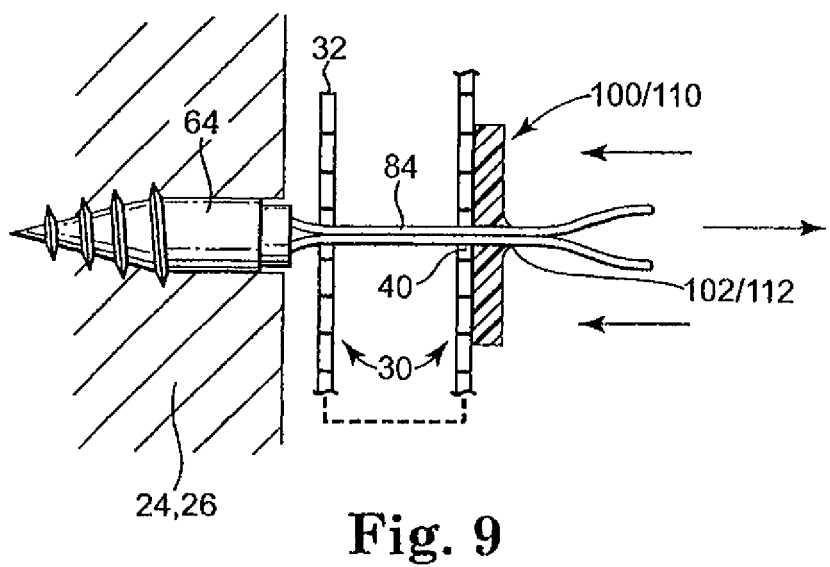
FIG. 9 is a side view in partial cross-section illustrating the passage of bone screw lines of a bone screw affixed to a descending pubic ramus through a mesh pore of the urethral sling and tensioning the urethral sling by drawing a line button of FIG. 7 or 8 over the lines and against the urethral sling.
Figure 10:
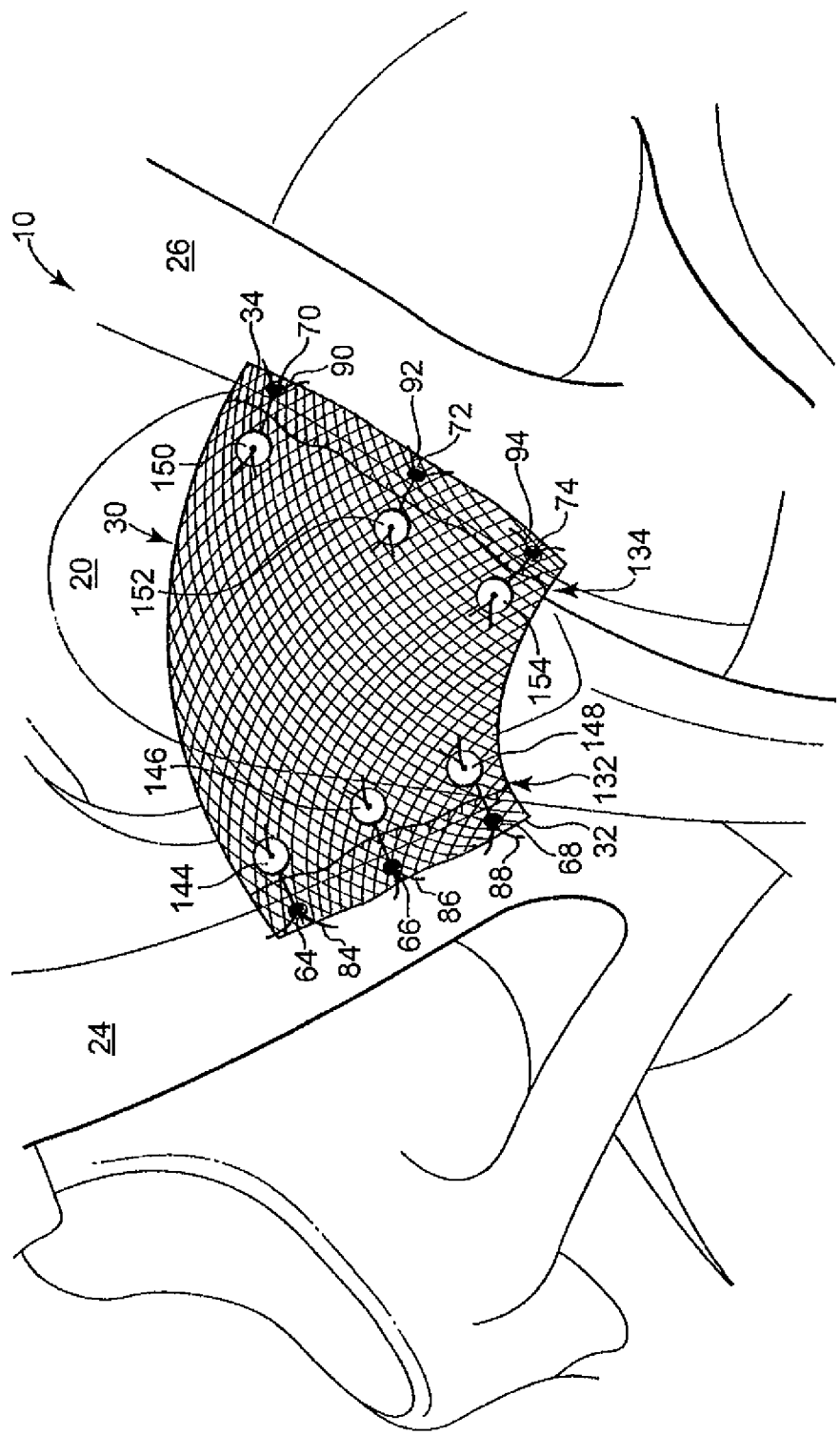
FIG. 10 is a schematic illustration of the urethral sling fixed to the bone screws with the bone screw lines drawn through the line buttons to form folds or creases in the urethral sling to adjust tension and obtain satisfactory urethral resistance.

The line buttons 100 and 110 are formed with centrally located button apertures 102 and 112, respectively, that are sized and shaped to receive and frictionally engage a bone screw line pair (or single line) as shown in FIGS. 9 and 10. The button aperture 102, 112 is shaped to allow a bone screw line to be inserted through it so that the line button 100, 110 may be advanced over the line pair toward the portion of the urethral sling 30 surrounding a selected mesh pore 40 that the line pair extends through as shown in FIG. 9 to apply force thereto. The button aperture 102, 112 is also shaped to maintain the applied force by resisting retraction of the line button 100, 110 along the line pair in the direction away from the bone screw 64 depicted in FIG. 9. Exemplary button aperture shapes are depicted in FIGS. 7 and 8 that form a pair of resilient flaps separated by an aperture that is smaller than the diameters of the bone screw lines (or line). The passage of the line pair 84 (or single line) widens the aperture and displaces the flaps away from the bone screw 64 as shown in FIG. 9 to resist slippage.

The line buttons 100 and 110 are preferably formed of a biocompatible material suitable for chronic implantation and having a resilience enabling the widening of the aperture between the flaps as depicted in FIG. 9 but resisting slippage. It will be understood that the button apertures 102 and 112 may take any other shape and size that allows advancement in one direction and resists retraction in the opposite direction.

In use, the lines of the line pairs 84, 86, 88 extending from the descending pubic ramus 24 may be each first passed though a selected adjacent mesh pore 40 adjacent the first sling end 32. The first sling free end 32 is then pressed against the descending pubic ramus 24. The free ends of each line of each line pairs 84, 86, 88 are sequentially grasped, drawn laterally toward the descending pubic ramus 26 and extended through a more remote mesh pore 40, whereby an edge portion of the urethral sling is disposed between the adjacent and remote mesh pores 40. In each case, a line button 100 or 110 is then applied over each of the line pairs 84, 86, 88 and advanced sufficiently toward the respective bone screws 64, 66, 68 to stay in place.

The procedure is then repeated to route the bone line pairs 90, 92 and 94 through adjacent and remote mesh pores 40 and to loosely apply a line button 100 or 110 over each of the line pairs 90, 92, 94 and advanced sufficiently toward the respective bone screws 70, 72, 74 to stay in place. The line buttons 100 or 110 over each of the bone line pairs 84, 86, 88, 90, 92, 94 are then selectively and sequentially advanced toward the respective bone screws 64, 66, 68, 70, 72, 74 to tension the urethral sling 30 intermediate the three line buttons 100 or 110 proximate the descending pubic ramus 24 and the three line buttons 100 or 110 proximate the descending pubic ramus 26. Testing for urethral resistance to leakage may be undertaken as described above to judge the sufficiency of the tensioning.

The application of the line buttons 100 or 110 and the tensioning of the urethral sling 30 are schematically depicted in FIG. 10. For convenience, the selected line buttons 100 or 110 applied over the bone screw lines 84, 86, 88, 90, 92, 94 are numbered respectively as 144, 146, 148, 150, 152, 154. The tensioning process may induce creases or folds 132 and 134 in the end portions of the urethral sling 30 adjacent the respective sling ends 32 and 34 and on either side of the tensioned intermediate portion of the urethral sling 30 as shown in FIG. 10. It will be understood that the free ends of the line pairs 84, 86, 88, 90, 92, 94 (or single lines) can be tied together or otherwise knotted with surgical knots over the line buttons 144, 146, 148, 150, 152, 154 if it is considered desirable to do so.

Figure 11:
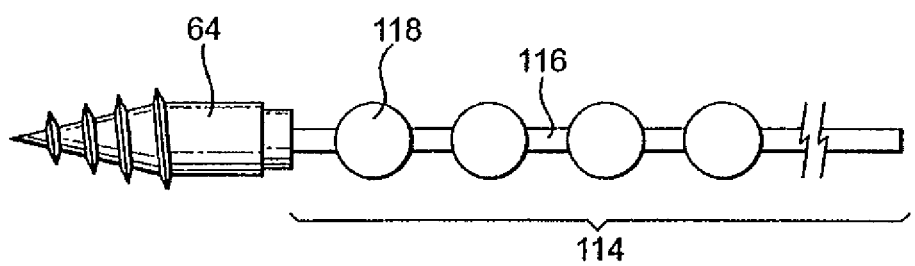
FIG. 11 is an expanded side view of a bone anchor, particularly a bone screw, with a bone screw line extending from the screw body shaped with periodic spherical fixation elements.
Figure 12:
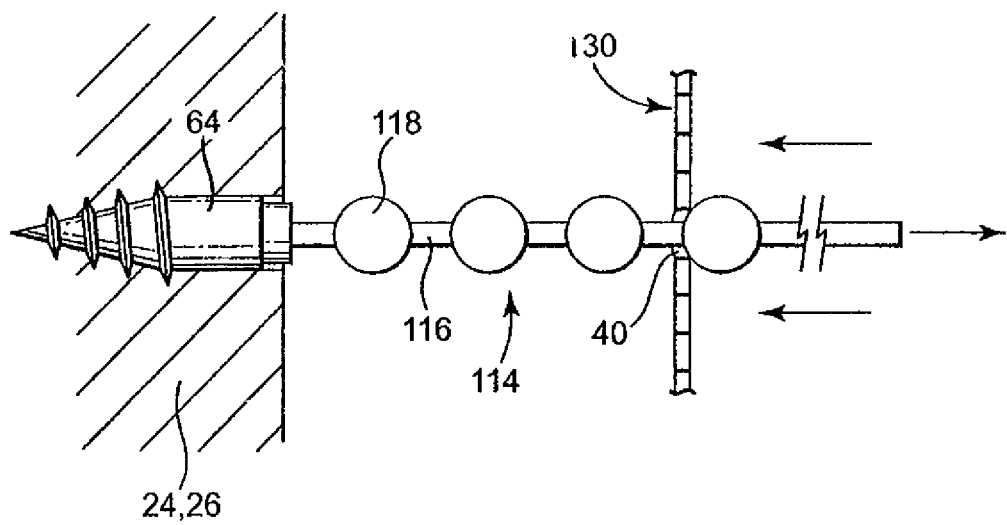
FIG. 12 is a side view illustrating the passage of the bone screw line of the bone screw of FIG. 11 affixed to a descending pubic ramus through a mesh pore of the urethral sling and tensioning the urethral sling by progressively drawing spherical fixation elements through a mesh pore to bear against the urethral sling.

A still further embodiment of the invention for applying tension to the urethral sling 30 in the manner depicted in FIG. 10 is illustrated in FIGS. 11 and 12. FIG. 11 illustrates a bone anchor, particularly a bone screw 64, with a bone screw line 114 extending from the screw body. The bone screw line 114 is shaped like a key chain having periodic, enlarged, substantially spherical line fixation elements 118 separated by reduced diameter link portions 116. The line fixation elements 118 may be attached to or formed integrally with the bone screw line 114. It will be understood that in this embodiment, the bone screw lines 84, 86, 88, 90, 92, 94 of each of the bone screws 64, 66, 68, 70, 72, 74 are shaped as exemplary bone screw line 114.

FIG. 12 illustrates the exemplary bone screw 64 of FIG. 11 affixed to a descending pubic ramus 24, 26, and the passage of the bone screw line 114 through a remote mesh pore 40 of the urethral sling 30. The urethral sling 30 is tensioned by progressively drawing spherical fixation elements 118 through the remote mesh pore 40 to advance the remote mesh pore 40 and surrounding portion of the urethral sling 30 toward the bone screw 64. Thus, the process described above with respect to the embodiment of FIGS. 7-10 is followed to tension the intermediate portion of the urethral sling and to induce the folds or creases 132 and 134 depicted in FIG. 10.

The tensioning of the intermediate portion of the urethral sling 30 should elongate the remote pores 40 that bear against the spherical fixation elements 118 so that the possibility of slippage by retraction of the spherical fixation elements 118 through the remote pores 40 is minimized. It will also be understood that a line button 100, 110 having a suitably sized and shaped button aperture 102, 112 may be supplied to fit over the spherical fixation elements 118 and rest in a reduced diameter link portion 116 to bear against the portion of the urethral sling surrounding the remote mesh pore 40 to reinforce the fixation and tensioning of the urethral sling 30.

Figure 13:
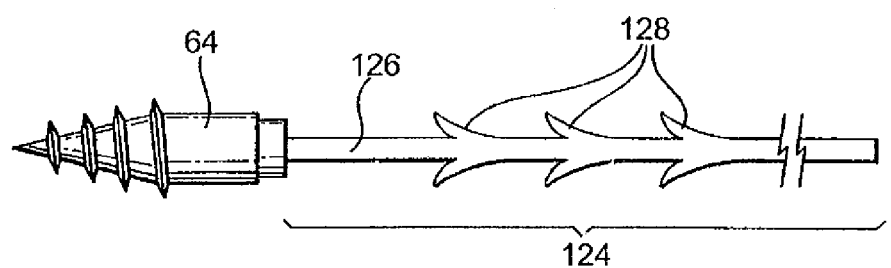
FIG. 13 is an expanded side view of a bone anchor, particularly a bone screw, with a bone screw line extending from the screw body shaped with periodic barbed fixation elements.
Figure 14:
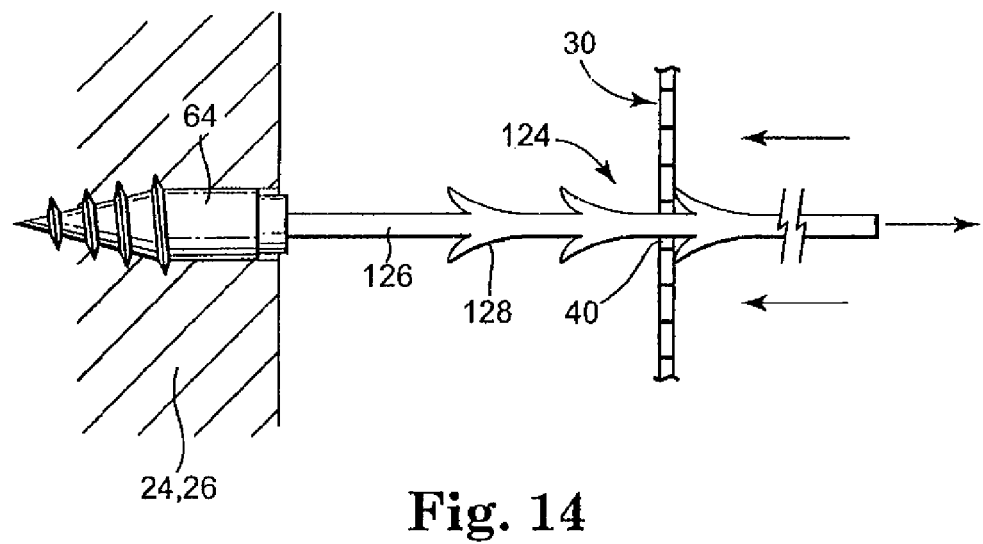
FIG. 14 is a side view illustrating the passage of the bone screw line of the bone screw of FIG. 13 affixed to a descending pubic ramus through a mesh pore of the urethral sling and tensioning the urethral sling by progressively drawing barbed fixation elements through a mesh pore to bear against the urethral sling.

Yet another embodiment of the invention for applying tension to the urethral sling 30 in the manner depicted in FIG. 10 is illustrated in FIGS. 13 and 14. FIG. 13 illustrates a bone anchor, particularly a bone screw 64, with a bone screw line 124 extending from the screw body. The bone screw line 124 is shaped to have periodic, enlarged, barbs 128 separated by reduced diameter link portions 126. The barb-shaped line fixation elements 128 may be attached to or formed integrally with the bone screw line 124. It will be understood that in this embodiment, the bone screw lines 84, 86, 88, 90, 92, 94 of each of the bone screws 64, 66, 68, 70, 72, 74 are shaped as exemplary bone screw line 124.

FIG. 14 illustrates the exemplary bone screw 64 of FIG. 13 affixed to a descending pubic ramus 24, 26, and the passage of the bone screw line 124 through a remote mesh pore 40 of the urethral sling 30. The urethral sling 30 is tensioned by progressively drawing barbs 128 through the remote mesh pore 40 to advance the remote mesh pore 40 and surrounding portion of the urethral sling 30 toward the bone screw 64. Thus, the process described above with respect to the embodiment of FIGS. 7-10 is followed to tension the intermediate portion of the urethral sling and to induce the folds or creases 132 and 134 depicted in FIG. 10.

The barbs 128 are relatively resilient and may spread to resist slippage of the tensioned urethral sling 30. It will also be understood that a line button 100, 110 having a suitably sized and shaped button aperture 102, 112 may be supplied to fit over the barbs 128 and rest in a reduced diameter link portion 126 to bear against the portion of the urethral sling 30 surrounding the remote mesh pore 40 to reinforce the fixation and tensioning of the urethral sling 30

FIG. 14 is a side view illustrating the passage of the bone screw line of the bone screw of FIG. 13 affixed to a descending pubic ramus through a mesh pore of the urethral sling and tensioning the urethral sling by progressively drawing barbed fixation elements through a mesh pore to bear against the urethral sling.

Various combinations of the above-described aspects of the invention may be made. For example, a line retainer, e.g., a line button 100, 110 of FIGS. 7 and 8 could be passed over the plicating line free ends 52 and 54 in lieu of the knots depicted in FIG. 6 to maintain the tension induced in the central portion of the urethral sling 30.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical surgical procedures that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

The invention claimed is:

1. A method of implanting a urethral sling to support the urethra comprising:
providing a urethral sling comprising:
a flexible sheet material extending between opposed first and second sling ends and bounded by opposed first and second sling sides; and
a plurality of pre-positioned, plicating line having a plicating line length extending between first and second plicating line free ends and passed through the flexible sheet material at first and second points displaced from the respective first and second sling free ends such that an intermediate portion of each plicating line extends across a central portion of the urethral sling intermediate first and second end portions of the urethral sling, the plicating lines being in substantially side-by-side relation between the first and second sling sides;
surgically affixing the first and second sling ends to extend across the urethra;
drawing one or more of the plicating line free ends together to induce tension in the first and second end portions and apply tension across the central portion of the urethral sling; and
tying the plicating line free ends; wherein:
the providing step comprises affixing the free ends of each plicating line through the sheet material at temporary retention points to hold the free ends against the flexible sheet material; and
the drawing step comprises releasing the free ends of each plicating line from the sheet material at the temporary retention points.

2. A method of implanting a urethral sling to support the urethra comprising:
providing a urethral sling comprising:
a flexible sheet material extending between opposed first and second sling ends and bounded by opposed first and second sling sides; and
at least one pre-positioned, plicating line having a plicating line length extending between first and second plicating line free ends and passed through the flexible sheet material at first and second points displaced from the respective first and second sling free ends such that an intermediate portion of the plicating line extends across a central portion of the urethral sling intermediate first and second end portions of the urethral sling;
surgically affixing the first and second sling ends to extend across the urethra;
drawing the plicating line free ends together to induce tension in the first and second end portions and apply tension across the central portion of the urethral sling; and
tying the plicating line free ends; wherein:
the providing step comprises affixing the free ends of each plicating line through the sheet material at temporary retention points to hold the free ends against the flexible sheet material; and
the drawing step comprises releasing the free ends of each plicating line from the sheet material at the temporary retention points.

3. A method of implanting a urethral sling to support the urethra comprising:
providing a urethral sling comprising:
a flexible sheet material extending between opposed first and second sling ends and bounded by opposed first and second sling sides; and at least one pre-positioned plicating line having a plicating line length extending between first and second plicating line free ends and passed through the flexible sheet material at first and second points displaced from the respective first and second sling free ends such that an intermediate portion of the plicating line extends across a central portion of the urethral sling intermediate first and second end portions of the urethral sling;

surgically affixing the first sling end to a right descending pubic rami of a patient and affixing the second sling end to a left descending pubic rami of the patient so that the central portion of the sling extends across the urethra;

drawing the plicating line free ends together to induce tension in the first and second end portions and apply tension across the central portion of the urethral sling; and tying the plicating line free ends together;

wherein the step of drawing the plicating line free ends together further comprises shortening a dimension of the central portion of the urethral sling.

* * * * *